United States Patent [19]

Wu

[11] Patent Number: 4,580,000

[45] Date of Patent: Apr. 1, 1986

[54] SELECTIVE SORPTION OF N-ALKYLBENZENE FROM A MIXTURE CONTAINING N-ALKYL AND SEC-ALKYL BENZENES

[75] Inventor: Margaret M. Wu, Belle Mead, N.J.

[73] Assignee: Mobil Oil Corporation, New York, N.Y.

[21] Appl. No.: 687,393

[22] Filed: Dec. 28, 1984

[51] Int. Cl.[4] .............................. C07C 7/12; B01J 8/44
[52] U.S. Cl. .................................... 585/828; 208/307
[58] Field of Search .................. 208/307; 585/828, 831

[56] References Cited

U.S. PATENT DOCUMENTS

| | | | |
|---|---|---|---|
| 3,437,704 | 4/1969 | Beckham et al. | 585/831 X |
| 3,484,500 | 12/1969 | Goldup et al. | 585/828 |
| 4,309,281 | 1/1982 | Dessau | 208/310 |
| 4,393,202 | 7/1983 | Kaeding | 585/467 |

FOREIGN PATENT DOCUMENTS

| | | |
|---|---|---|
| 031676 | 12/1979 | European Pat. Off. . |
| 197803 | 3/1978 | Fed. Rep. of Germany . |
| 8005829 | 10/1980 | Netherlands . |

OTHER PUBLICATIONS

Namba et al, "Separation of P-Isomers from Disubstituted Benzenes by Means of Shape-Selective Adsorption on Mordenite and ZSM-5 Zeolites", *Zeolites*, 4(1), pp. 77–80 (1984).

*Primary Examiner*—John Doll
*Assistant Examiner*—Glenn A. Caldarola
*Attorney, Agent, or Firm*—Alexander J. McKillop; Michael G. Gilman; Edward F. Kenehan, Jr.

[57] ABSTRACT

There is provided a method for the selective sorption of n-alkylbenzene, such as n-propylbenzene, from an alkylbenzene mixture, such as a mixture of n-propylbenzene and isopropylbenzene, with an oxide impregnated ZSM-5 sorbent. This method may be particularly useful in the purification of cumene product streams.

17 Claims, No Drawings

SELECTIVE SORPTION OF N-ALKYLBENZENE FROM A MIXTURE CONTAINING N-ALKYL AND SEC-ALKYL BENZENES

BACKGROUND

This invention relates to a method for the selective sorption of n-alkylbenzene from an alkylbenzene mixture with an oxide impregnated ZSM-5 sorbent.

The separation of n-alkylbenzenes from sec-alkylbenzenes may be difficult. More particularly, for example, n-propylbenzene cannot readily be separated from isopropylbenzene (i.e., cumene) by distillation.

The Kaeding U.S. Pat. No. 4,393,262, the entire disclosure of which is expressly incorporated herein by reference, describes a process for the selective production of isopropylbenzene by propylating benzene over a ZSM-12 catalyst. However, even with such selective preparations an undesirable amount of n-propylbenzene may be cogenerated.

SUMMARY

According to one aspect of the invention, there is provided a method for selectively sorbing n-alkylbenzene from an alkylbenzene mixture containing both n-alkylbenzene and sec-alkylbenzene, said method comprising contacting said alkylbenzene mixture with ZSM-5 having impregnated in the pore space thereof at least one difficultly reducible oxide, said contacting taking place under sufficient contacting conditions whereby n-alkylbenzene is sorbed into the pore space of said ZSM-5.

According to another aspect of the invention, there is provided a method for selectively sorbing n-propylbenzene from a propylbenzene mixture containing both n-propylbenzene and isopropylbenzene, said method comprising contacting said propylbenzene mixture with ZSM-5 having impregnated in the pore space thereof magnesium oxide, said contacting taking place under sufficient conditions whereby n-alkylbenzene is sorbed into the pore space of said ZSM-5.

According to another aspect of the invention, there is provided an improved process for the propylation of benzene with selective production of isopropylbenzene, said process comprising contacting mixtures of benzene and propylene with a crystalline zeolite catalyst at a temperature of between about 100° C. and the critical temperature, and a pressure of between about $10^5$ N/m$^2$ and $6 \times 10^6$ N/m$^2$, said zeolite being characterized by a silica/alumina mole ratio of at least about 12 and a constraint index within the approximate range of 1 to 12, said zeolite being ZSM-12, wherein the improvement is for removing n-propylbenzene impurities from said isopropylbenzene product, said improvement comprising contacting said isopropylbenzene product wth ZSM-5 having impregnated in the pore space thereof at least one difficulty reducible oxide, said contacting taking place under sufficient contacting conditions whereby n-propylbenzene is sorbed into the pore space of said ZSM-5.

DETAILED DESCRIPTION

The sorbent suitable for use in accordance with the present invention is ZSM-5. ZSM-5 may be identified by a characteristic X-ray diffraction pattern and is described in U.S. Pat. No. 3,702,886, the entire disclosure of which is incorporated herein by reference.

When ZSM-5 is prepared in the presence of organic cations, the intracrystalline free space of the freshly prepared ZSM-5 is occupied by organic cations from the forming solution. These organic cations are preferably removed from the ZSM-5. This removal may be accomplished by heating the ZSM-5 in an inert atmosphere at 540° C. for one hour, for example, followed by base exchange with ammonium salts followed by calcination at 540° C. in air. More generally, it is desirable to remove these organic cations by base exchange with ammonium salts followed by calcination in air at about 540° C. for from about 15 minutes to about 24 hours.

Although ZSM-5 zeolites with a silica to alumina ratio of at least 12 are useful, it is preferred to use ZSM-5 zeolites having higher ratios of at least about 30.

When synthesized in the alkali metal form, the ZSM-5 zeolite is conveniently converted to the hydrogen form, generally by intermediate formation of the ammonium form as a result of ammonium ion exchange and calcination of the ammonium form to yield the hydrogen form. In addition to the hydrogen form, referred to herein as HZSM-5, other forms of the ZSM-5 zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired sorption process, it may be desirable to incorporate the above described crystalline ZSM-5 zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite includes those of the montmorillonite and kaolin families, which families include the sub-bentonites and the kaolins commonly known as Dixie, McNamee-Georgia and Flordia clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-alumina-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

In order to enhance the sorption selectivity of the ZSM-5 zeolites, the pore space of the zeolites is impregnated with difficulty reducible oxides. Oxides of this type can include oxides of phosphorus as well as those oxides of the metals of Groups IA, IIA, IIIA, IVA, VA, VIA, VIIA, VIIIA, IB, IIB, IVB, or VB of te Periodic Chart of the Elements (Fisher Scientific Company, Catalog No. 5-702-10) which serve to enhance the sorption selectivity properties of the ZSM-5 modified therein. The difficultly reducible oxides most commonly employed to modify the selectivity properties of the ZSM-5 zeolites are oxides of phosphorus and magnesium. Thus, the ZSM-5 zeolites can be treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such ZSM-5 zeolites at least in part in the form of phosphorus oxide in an amount of from about 0.25% to about 25% by weight of the catalyst composition, preferably from about 0.7% to about 15% by weight. Such incorporation can be readily effected by contacting the zeolite composite with a solution of an appropriate phosphorus compound, followed by drying and calcining to convert phosphorus in the zeolite to its oxide form. Preferred phosphorus-containing compounds include diphenyl phosphine chloride, trimethylphosphite and phosphorus trichloride, phosphoric acid, phenyl phosphine oxychloride, trimethylphosphate, diphenly phosphinous acid, diphenyl phosphinic acid, diethylchlorothiophosphate, methyl acid phosphate and other alcohol-$P_2O_5$ reaction products. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3-5 hours but may be extended to 24 hours or longer.

Magnesium oxide is another preferred difficultly reducible oxide which can be incorporated with the ZSM-5 zeolite in a manner similar to that employed with phosphorus. Magnesium can comprise from about 0.25% to 25% by weight preferably from about 1% to 15% by weight present at least in part as magnesium oxide. As with phosphorus, magnesium oxide incorporated is effected by contacting the zeolite with an appropriate magnesium compound followed by drying and calcining to convert magnesium to the zeolite to its oxide form. Preferred magnesium-containing compounds include magnesium nitrate and magnesium acetate. Calcination times and temperatures are generally the same as recited hereinbefore for calcination of phosphorus-containing catalysts.

In addition to treatment of the ZSM-5 zeolites to incorporate phosphorus and/or magnesium oxides as hereinbefore described in detail, such zeolites may also be modified in a substantially similar manner to incorporate thereon a variety of other oxide materials to enhance sorption selectivity. Such oxide materials includes oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group IVB metals (U.S. Pat. No. 4,278,827); Group VIA metals (U.S. Pat. No. 4,259,537); Group IA elements (U.S. Pat. No. 4,329,533); cadmium (U.S. Pat. No. 4,384,155); iron and/or cobalt (U.S. Pat. No. 4,380,685); Group IIIB metals (U.S. Pat. No. 4,276,437); Group IVA metals (U.S. Pat. No. 4,320,620); Group VA metals (U.S. Pat. No. 4,302,621); and Group IIIA elements (U.S. Pat. No. 4,302,622).

The ZSM-5 sorbents suitable for use in accordance with the present invention preferably have an average particle size of at least 1 micron. As referred to herein, the expression, average particle size, shall refer to the shortest diffusional path length of the particles, i.e., the shortest cross sectional dimension of the particles.

In accordance with the present invention the weight ratio of n-alkylbenzene sorbed to sec-alkylbenzene sorbed may be, e.g., at least 7:1 or even at least 12:1.

It will be readily understood that the impregnated zeolites suitable for use in accordance with the present invention are quite distinguished from zeolites which are merely ion exchanged. In ion exchanged zeolites the number of positive charges from the ion exchange material may be at most, substantially equal to the number of cationic sites in the framework of the zeolite. On the other hand, the number of positive charges in the cations of the difficultly reducible oxide impregnant of the present invention may or may not exceed the number of cationic sites in the framework of the ZSM-5. Accordingly, the ratio of the number of positive charges in the cations of the difficultly reducible oxide impregnant to the number of cationic sites in the framework of the ZSM-5 may be as small as, e.g., 0.1 and may be as large as, e.g., 2 or greater or even 5 or greater. It will be further understood that the number of positive charges in the cations of the difficultly reducible oxide impregnant equals the product of the number of these cations multiplied by the valency of these cations.

The optimal contacting conditions suitable for use in accordance with the present invention may be arrived at by a routine trial and error procedure, especially with reference to the specific embodiments of the Example and Comparative Examples set forth hereinafter. The optimal contacting conditions may vary, e.g., in accordance with the nature of the sorbent and the alkylbenzene mixture used. In some instances, room temperature and atmospheric pressure may be satisfactory. However, in other circumstances it may be desirable to use an elevated pressure and/or an elevated temperature, e.g., a temperature from about 50 to about 100 degrees C.

The alkylbenzene mixture may be in either the liquid or the vapor phase when contacted with the impregnated ZSM-5.

The alkylbenzene mixture which may be contacted with the impregnated ZSM-5 sorbents in accordance with the present invention may comprise, e.g., $C_3-C_6$ alkylbenzenes, a particularly suitable alkylbenzene mixture is a mixture of isopropylbenzene and n-propylbenzene. The alkylbenzene mixture may be contacted with the impregnated ZSM-5 sorbent alone or in the presence of inert diluents.

The amount of impregnated ZSM-5 used in accordance with the present invention should be sufficient to sorb the desired amount of n-alkylbenzene. The weight ratio of said n-alkylbenzene in said alkylbenzene mixture to said ZSM-5 may be, e.g., about 1:1 or less.

The alkylbenzene mixture may contain, e.g., from about 0.1 to about 50 percent by weight of n-alkylbenzene.

Selective sorption experiments were carried out by mixing a solution containing n-alkylbenzene, sec-alkylbenzene and an internal standard, adamantane, with a proper amount of zeolites at room temperature or on a steam bath. The residual product was analyzed periodically on G.C. with a 25 meter SE-30 fused silica capillary column.

COMPARATIVE EXAMPLE A

A solution containing 1.535% i-proplybenzene (IPB), 1.62% n-propylbenzene (NPB) and 1.555% adamantane (ADM) in triisopropylbenzene (TIPB), 2.0 grams, was added to 1.0 gram of the hydrogen form of ZSM-5 (i.e., HZSM-5). By the hydrogen form of ZSM-5 is meant non-impregnated ZSM-5 having essentially all of the cationic sites occupied by hydrogen. The change of solution composition as a function of time is shown in Table 1. The amount of NPB in total propylbenzene (PB) fraction decreased from 51.3% in the starting material to 9.8% after 60 minutes. The ratio of NPB absorbed ($\%A_{NPB}$) to IPB absorbed ($\%A_{IPB}$), R, is always greater than 1. This indicated that NPB was more selectively absorbed by HZSM-5 than IPB.

TABLE 1

| Catalyst: HZSM-5 | | Time, minutes | | | | |
|---|---|---|---|---|---|---|
| Wt % Compositions | SM | 0.5 | 5 | 10 | 30 | 60 |
| NPB | 1.620 | 1.704 | 0.744 | 0.449 | 0.159 | 0.056 |
| IPB | 1.535 | 1.833 | 1.156 | 0.915 | 0.653 | 0.517 |
| ADM | 1.555 | 1.902 | 1.846 | 1.888 | 1.924 | 1.991 |
| % NPB in PB | 51.3 | 48.2 | 39.5 | 32.9 | 19.6 | 9.8 |
| $R = \frac{\% A_{NPB}}{\% A_{IPB}}$ | — | 6.1 | 1.7 | 1.5 | 1.4 | 1.3 |

EXAMPLE 1

Two grams of the solution, as in Example 1, was added to 1 gram of magnesium oxide impregnated ZSM-5 (i.e., MgZSM-5). The magnesium modified ZSM-5 did not sorb much NPB or IPB at room temperature after 60 minutes in contact. The mixture was then heated to 60°–70° C. on a steam bath. NPB was selectively absorbed by the MgZSM-5 sorbent. Results are shown in Table 2. The amount of NPB in total propylbenzene fraction decreased from 51.3% to 18.3% after 30 hours. R is always greater than 1 for all the runs. The results clearly showed that NPB was selectively removed, the degree of selectivity being greater than that shown in Comparative Example A. The average particle size of the MgZSM-5 sorbent of this Example was within the approximate range of from about 1 to about 5 microns.

TABLE 2

| Catalyst: MgZSM-5 | | | | | | | | | | |
|---|---|---|---|---|---|---|---|---|---|---|
| Temperature, °C. | — | RT | RT | 70 | 70 | 70 | 70 | 70 | 70 | |
| Time | SM | 10 | 60 | 20 | 40 | 180 | 210 | 300 | 30 hrs | |
| Wt % Composition | | | | | | | | | | |
| NPB | 1.620 | 1.613 | 1.825 | 1.396 | 1.267 | 1.013 | 0.902 | 0.935 | 0.356 | |
| IPB | 1.535 | 1.589 | 1.783 | 1.640 | 1.607 | 1.656 | 1.575 | 1.839 | 1.594 | |
| ADM | 1.555 | 1.693 | 1.921 | 1.751 | 1.726 | 1.787 | 1.677 | 1.931 | 1.573 | |
| % NPB in PB | 51.3 | 50.4 | 50.6 | 46.0 | 44.1 | 38.0 | 3.64 | 33.7 | 18.3 | |
| $R = \frac{\% A_{NPB}}{\% A_{IPB}}$ | — | 1.9 | 1.5 | 4.6 | 5.2 | 7.5 | 9.9 | 15.3 | infinity | |

COMPARATIVE EXAMPLE B

NaZSM-5 was prepared by ion exchanging HZSM-5 of $SiO_2/Al_2O_3$ of 70/1 with quantitative amounts of aqueous $NaHCO_3$ solution. The resulting NaZSM-5 contained 1.43% by weight of sodium. Two grams of the solution used in Comparative Example A and 1 gram of the calcined NaZSM-5 were mixed at room temperature. The solution composition, analyzed periodically, is shown in Table 3. In all the Runs, the amount of n-propylbenzene absorbed was higher than the amount of isopropylbenzene (R>1). The amount of n-propylbenzene decreased from 51.3% in the starting material to 4.7% after 49 minutes.

The averagae particle size of the NaZSM-5 sorbent of this Comparative Example was within the appropriate range of from about 0.5 to about 1 micron.

TABLE 3

| Catalyst: NaZSM-5 | | Time | | | | |
|---|---|---|---|---|---|---|
| Wt % Compositions | SM | 0.5 | 6 | 12 | 37 | 49 |
| NPB | 1.193 | 0.958 | 0.135 | 0.039 | 0.008 | 0.009 |
| IPB | 1.129 | 1.110 | 0.459 | 0.310 | 0.193 | 0.182 |
| ADM | 1.140 | 1.159 | 1.171 | 1.199 | 1.177 | 1.205 |
| % NPB in PB | 51.4 | 46.6 | 22.727 | 11.2 | 4.0 | 4.7 |
| $R = \frac{\% A_{NPB}}{\% A_{IPB}}$ | — | 12.3 | 1.5 | 1.3 | 1.2 | 1.2 |

COMPARATIVE EXAMPLE C 3A molecular sieve, available from Chemical Dynamic Corporation, ZSM-4 and ZSM-12 were also tested for selective sorption of NPB, using the same solution as in Comparative Example A. Results are shown in Tables 4, 5 and 6. In all runs, the amount of NPB sorbed was mush less than in Example 1 and Comparative Examples A and B. The total amount of % NPB in the solution did not change much.

TABLE 4

| Catalyst: 3A molecular sieve | | Time | | | | |
|---|---|---|---|---|---|---|
| Wt % Compositions | SM | 0 | 5 | 10 | 30 | 60 |
| NPB | 1.620 | 1.933 | 1.913 | 1.841 | 1.737 | 1.961 |
| IPB | 1.535 | 1.859 | 1.878 | 1.807 | 1.719 | 2.015 |
| ADM | 1.555 | 1.844 | 1.889 | 1.851 | 1.783 | 2.004 |
| % NPB in PB | 51.3 | 51.0 | 50.5 | 50.5 | 50.4 | 49.3 |

TABLE 5

| Catalyst: ZSM-4 | | Time | | | |
|---|---|---|---|---|---|
| Wt % Compositions | SM | 0 | 10 | 30 | 60 |
| NPB | 1.620 | 1.787 | 1.384 | 1.729 | 1.691 |
| IPB | 1.535 | 1.710 | 1.411 | 1.766 | 1.681 |
| ADM | 1.555 | 1.727 | 1.563 | 1.958 | 1.940 |
| % NPB in PB | 51.3 | 51.1 | 49.5 | 49.5 | 50.1 |

TABLE 6

| Catalyst: ZSM-12 | | Time | | | | |
|---|---|---|---|---|---|---|
| Wt % Compositions | SM | 0.5 | 5 | 10 | 30 | 60 |
| NPB | 1.620 | 1.896 | 1.606 | 1.558 | 2.566 | 1.315 |
| IPB | 1.535 | 1.865 | 1.719 | 1.681 | 2.733 | 1.573 |
| ADM | 1.555 | 1.936 | 1.891 | 1.893 | 2.976 | 1.875 |
| % NPB in PB | 50.3 | 50.4 | 48.3 | 48.1 | 48.4 | 45.5 |

COMPARATIVE EXAMPLE D

The NaZSM-5 catalyst was prepared as in Comparative Example B. 0.5 gram of the catalyst was added to a solution, 1.0 gram, containing 2.019% n-butybenzene (NBB), 2.263% sec-butylbenzene (SBB), 1.786% adamantane (ADM) in triisopropylbenzene solvent. The solution composition was analyzed periodically and is summarized in Table 7. The amount of NBB in butylbenzene (BB) fraction decreased from 47.2% in the starting solution to 1.5% after 164 minutes in contact with NaZSM-5. This indicates that the n-alkylbenzene was selectively absorbed by NaZSM-5.

TABLE 7

| Catalyst: NaZSM-5 | | | | | | | | |
|---|---|---|---|---|---|---|---|---|
| Time | SM | 0.5 | 7 | 17 | 24 | 35 | 64 | 164 |
| Wt % Composition | | | | | | | | |
| NBB | 2.019 | 1.842 | 0.442 | 0.277 | 0.163 | 0.096 | 0.062 | 0.038 |
| SBB | 2.263 | 2.240 | 1.662 | 1.707 | 1.775 | 1.629 | 1.561 | 2.581 |
| ADM | 1.786 | 1.772 | 1.814 | 1.965 | 2.116 | 1.938 | 1.833 | 2.677 |
| % NBB in BB | 47.2 | 45.1 | 21.0 | 14.0 | 6.2 | 5.6 | 3.8 | 1.5 |
| $R = \frac{\% A_{NBB}}{\% A_{SBB}}$ | — | 41 | 2.8 | 2.8 | 2.8 | 2.8 | 3.0 | 2.9 |

COMPARATIVE EXAMPLE E

A solution, containing 0.0506% NPB in 98.93% IPB, two grams, was added to 1 gram HZSM-5 catalyst. After 10 minutes, the content of NPB decreased to 0.009%, and the purity of IPB increased to 99.803%. The average particle size of the HZSM-5 sorbent of this Comparative Example was within the approximate range of from about 0.5 to about 1 micron.

COMPARATIVE EXAMPLE F

Two grams of the same solution used in Comparative Example E was added to one gram NaZSM-5, prepared as in Comparative Example B. After six minutes, the content of NPB decreased to 0.017%, and the purity of IPB increased to 99.632%.

COMPARATIVE EXAMPLE G

Two grams of the solution containing 0.975% NPB in 98.387% IPB was added to one gram HZSM-12 catalyst. After 16 hours in contact, the amount of NPB was 0.891 and purity of IPB was 98.757. This catalyst was not as selective for NPB sorption as in Comparative Examples E and F.

What is claimed is:

1. A method for selectively sorbing n-alkylbenzene from an alkylbenzene mixture containing both n-alkylbenzene and sec-alkylbenzene, said method comprising contacting said alkylbenzene mixture with ZSM-5 having impregnated in the pore space thereof at least one group IIA metal oxide, said contacting taking place under sufficient contacting conditions whereby n-alkylbenzene is sorbed into the pore space of said ZSM-5.

2. A method according to claim 1, wherein the weight ratio of n-alkylbenzene sorbed to sec-alkylbenzene sorbed is at least 7:1.

3. A method according to claim 1 wherein the product of the number of cations multiplied by the valency of said cations in said group IIA metal oxide exceeds the number of cationic sites in the framework of said ZSM-5 by a factor of at least 2.

4. A method according to claim 1, wherein said group IIA metal oxide is magnesium oxide.

5. A method according to claim 1, wherein said ZSM-5 is incorporated into a binder therefor.

6. A method according to claim 1, wherein said contacting conditions include a pressure of about one atmosphere.

7. A method according to claim 1, wherein said alkylbenzene mixture is in the liquid phase.

8. A method according to claim 1, wherein said alkylbenzene mixture is in the vapor phase.

9. A method according to claim 1, wherein said alkylbenzene mixture is a mixture of isopropylbenzene and n-propylbenzene.

10. A method according to claim 1, wherein the weight ratio of said n-alkylbenzene in said alkylbenzene mixture to said ZSM-5 is about 1:1 or less.

11. A method according to claim 1, wherein said alkylbenzene mixture contains from about 0.1 to about 50 percent by weight of n-alkylbenzene.

12. A method for selectively sorbing n-propylbenzene from a propylbenzene mixture containing both n-propylbenzene and isopropylbenzene, said method comprising contacting said propylbenzene mixture with ZSM-5 having impregnated in the pore space thereof magnesium oxide, said contacting taking place under sufficient conditions whereby n-alkylbenzene is sorbed into the pore space of said ZSM-5.

13. In a process for the propylation of benzene with selective production of isopropylbenzene, said process comprising contacting mixtures of benzene and propylene with a crystalline zeolite catalyst at a temperature of between about 100° C. and the critical temperature, and a pressure of between about $10^5$ N/m$^2$ and $6 \times 10^6$ N/m$^2$, said zeolite being characterized by a silica/alumina mole ratio of at least about 12 and a constraint index within the approximate range of 1 to 12, said zeolite being ZSM-12, the improvement for removing n-propylbenzene impurities from said isopropylbenzene product, said improvement comprising contacting said isopropylbenzene product with ZSM-5 having impregnated in the pore space thereof at least one group IIA metal oxide said contacting taking place under sufficient contacting conditions whereby n-propylbenzene is sorbed into the pore space of said ZSM-5.

14. A method according to claim 13, wherein the weight ratio of n-propylbenzene sorbed to isopropylbenzene sorbed is at least 7:1.

15. A method according to claim 13, wherein the product of the number of cations multiplied by the valency of said cations in said group IIA metal oxide exceeds the number of cationic sites in the framework of said ZSM-5 by a factor of at least 2.

16. A method according to claim 13, wherein said group IIA metal oxide is magnesium oxide.

17. A method according to claim 13, wherein said ZSM-5 is incorporated into a binder therefor.

* * * * *